US010882027B2

(12) United States Patent
Nadolny et al.

(10) Patent No.: US 10,882,027 B2
(45) Date of Patent: Jan. 5, 2021

(54) PROCESS FOR PRODUCING AN OLIGOMERIZATION CATALYST

(71) Applicant: Evonik Operations GmbH, Essen (DE)

(72) Inventors: Fabian Nadolny, Arnsberg (DE); Stephan Peitz, Oer-Erkenschwick (DE); Guido Stochniol, Haltern Am See (DE); Robert Franke, Marl (DE); Thomas Quandt, Marl (DE)

(73) Assignee: Evonik Operations GmbH, Essen (DE)

( * ) Notice: Subject to any disclaimer, the term of this patent is extended or adjusted under 35 U.S.C. 154(b) by 61 days.

(21) Appl. No.: 16/293,702

(22) Filed: Mar. 6, 2019

(65) Prior Publication Data

US 2019/0283005 A1    Sep. 19, 2019

(30) Foreign Application Priority Data

Mar. 14, 2018 (EP) .................... 18161764

(51) Int. Cl.
| | | |
|---|---|---|
| *B01J 23/78* | (2006.01) | |
| *B01J 21/12* | (2006.01) | |
| *B01J 35/02* | (2006.01) | |
| *B01J 35/10* | (2006.01) | |
| *B01J 37/00* | (2006.01) | |
| *B01J 37/02* | (2006.01) | |
| *B01J 37/04* | (2006.01) | |
| *B01J 37/08* | (2006.01) | |
| *C07C 2/10* | (2006.01) | |
| *C07C 2/24* | (2006.01) | |
| *C07C 2/30* | (2006.01) | |
| *B01J 23/755* | (2006.01) | |
| *B01J 35/00* | (2006.01) | |

(52) U.S. Cl.
CPC ............... *B01J 23/78* (2013.01); *B01J 21/12* (2013.01); *B01J 23/755* (2013.01); *B01J 35/002* (2013.01); *B01J 35/023* (2013.01); *B01J 35/1019* (2013.01); *B01J 37/0018* (2013.01); *B01J 37/0063* (2013.01); *B01J 37/0201* (2013.01); *B01J 37/0236* (2013.01); *B01J 37/04* (2013.01); *B01J 37/08* (2013.01); *C07C 2/10* (2013.01); *C07C 2/24* (2013.01); *C07C 2/30* (2013.01); *C07C 2521/12* (2013.01); *C07C 2523/755* (2013.01); *C07C 2527/053* (2013.01); *C07C 2527/25* (2013.01); *C07C 2531/12* (2013.01)

(58) Field of Classification Search
CPC ........ B01J 23/78; B01J 23/755; B01J 35/002; B01J 21/12; B01J 35/023; B01J 35/1019; B01J 37/0018; B01J 37/0063; B01J 37/0201; B01J 37/0236; B01J 37/04; B01J 37/08; B01J 27/24; B01J 31/1805; B01J 35/109; B01J 2231/20; C07C 2/10; C07C 2/24; C07C 2/30; C07C 2521/12; C07C 2523/755; C07C 2527/053; C07C 2527/25; C07C 2531/12; C07C 2527/24; C07C 2531/18

See application file for complete search history.

(56) References Cited

U.S. PATENT DOCUMENTS

| | | | | |
|---|---|---|---|---|
| 2,581,228 | A | * | 1/1952 | Bailey ................ C08F 4/26 502/259 |
| 3,557,242 | A | | 1/1971 | Sampson et al. |
| 5,177,282 | A | * | 1/1993 | Nierlich ............... C07C 7/13 585/329 |
| 5,849,972 | A | | 12/1998 | Vicari et al. |
| 7,939,597 | B2 | | 5/2011 | Bub et al. |
| 8,198,481 | B2 | | 6/2012 | Kuppinger et al. |
| 8,258,249 | B2 | | 9/2012 | Bub et al. |
| 8,293,941 | B2 | | 10/2012 | Kuppinger et al. |
| 8,481,784 | B2 | | 7/2013 | Kuppinger et al. |
| 8,524,945 | B2 | | 9/2013 | Stochniol et al. |
| 8,895,683 | B2 | | 11/2014 | Kuppinger et al. |
| 9,676,805 | B2 | | 6/2017 | Dyballa et al. |
| 9,845,276 | B2 | | 12/2017 | Franke et al. |
| 9,856,184 | B2 | | 1/2018 | Stochniol et al. |
| 10,155,200 | B2 | | 12/2018 | Geilen et al. |
| 10,189,755 | B2 | | 1/2019 | Reeker et al. |
| 10,196,327 | B2 | | 2/2019 | Stochniol et al. |
| 2006/0276334 | A1 | | 12/2006 | Balduf et al. |
| 2009/0068440 | A1 | | 3/2009 | Bub et al. |
| 2016/0257634 | A1 | | 9/2016 | Dyballa et al. |

(Continued)

FOREIGN PATENT DOCUMENTS

| | | |
|---|---|---|
| DE | 10 2009 027408 A1 | 1/2011 |
| FR | 3 054 455 A1 | 2/2018 |

(Continued)

OTHER PUBLICATIONS

German language European Search Report dated Aug. 7, 2019 in EP 19162261 (2 pages).

(Continued)

*Primary Examiner* — Ali Z Fadhel
(74) *Attorney, Agent, or Firm* — Taylor English Duma LLP; Philip P. McCann

(57) ABSTRACT

The invention relates to a process for producing an oligomerization catalyst comprising nickel oxide and a silicon-alumina support material, wherein the silica-alumina support material is in the ammonium form. The present invention further relates to a process for oligomerization of C3- to C6-olefins using the oligomerization catalyst produced according to the invention.

20 Claims, No Drawings

(56) References Cited

U.S. PATENT DOCUMENTS

2018/0072647 A1    3/2018    Stochniol et al.
2018/0126361 A1    5/2018    Klasovslcy et al.

FOREIGN PATENT DOCUMENTS

| JP | 2014151253 A1 | 8/2014 |
| WO | 95/14647 A1 | 6/1995 |
| WO | 2010/117539 A2 | 10/2010 |
| WO | 2014/123243 A1 | 8/2014 |
| WO | 2016/067033 A1 | 5/2016 |

OTHER PUBLICATIONS

Harms et al., "Propene oligomerization over nickel-loaded silica-alumina," Fuel Processing Technology, Copyright Mar. 1989, Elsevier BV, NL, Bd. 21, Nr. 3, pp. 231-243 (13 pages).
Hensen et al., "Acidity Characterization of Amorphous Silica-Alumina," Journal of Physical Chemistry C, copyright Sep. 2012, Bd. 116, Nr. 40, pp. 21416-21429 (14 pages).
Fridag et al., U.S. Appl. No. 16/203,929, filed Nov. 29, 2018.
Fridag et al., U.S. Appl. No. 16/204,263, filed Nov. 29, 2018.
Fridag et al., U.S. Appl. No. 16/204,572, filed Nov. 29, 2018.
Nadolny et al., U.S. Appl. No. 16/291,144, filed Mar. 4, 2019.
Nadolny et al., U.S. Appl. No. 16/293,717, filed Mar. 6, 2019.
Nadolny et al., U.S. Appl. No. 16/298,561, filed Mar. 11, 2019.
Nadolny et al., U.S. Appl. No. 16/293,859, filed Mar. 6, 2019.

\* cited by examiner

PROCESS FOR PRODUCING AN OLIGOMERIZATION CATALYST

CROSS REFERENCE TO RELATED APPLICATIONS

This application is a 35 U.S.C. § 119 patent application which claims the benefit of European Application No. 18161764.8 filed Mar. 14, 2018, which is incorporated herein by reference in its entirety.

FIELD

The present invention relates to a process for producing an oligomerization catalyst comprising nickel oxide and a silicon-alumina support material, wherein the silica-alumina support material is in the ammonium form. The present invention further relates to a process for oligomerization of C3- to C6-olefins using the oligomerization catalyst produced according to the invention.

BACKGROUND

Oligomerization is generally understood as meaning the reaction of unsaturated hydrocarbons with themselves to form correspondingly longer-chain hydrocarbons, the so-called oligomers. Thus, for example, an olefin having six carbon atoms (hexene) can be formed by oligomerization of two olefins having three carbon atoms. The oligomerization of two molecules with one another is also referred to as dimerization.

The resulting oligomers are intermediates that are used, for example, for producing aldehydes, carboxylic acids and alcohols. The oligomerization of olefins is carried out on a large industrial scale either in the homogeneous phase using a dissolved catalyst or heterogeneously over a solid catalyst, or else with a biphasic catalyst system.

In the case of the heterogeneously catalysed processes, oligomerization over acidic oligomerization catalysts has long been known. Systems employed industrially include for example zeolites or phosphoric acid on a support. Isomeric mixtures of branched olefins are obtained here. For non-acidic, heterogeneously catalyzed oligomerization of olefins with high dimer selectivity, nickel compounds on support materials are frequently employed in industry. Thus WO 95/14647 A1 describes a nickel catalyst comprising a support material consisting of the components titanium oxide and/or zirconium oxide, silicon oxide and optionally aluminium oxide for olefin oligomerization. Over these catalysts, mixtures of linear butenes are oligomerized to C8-olefins with a selectivity of below 75%.

Various processes for the production of oligomerization catalysts are known in the prior art. For example, WO 95/14647 A1 discloses a process for producing an oligomerization catalyst in which the individual components are precipitated from a solution. The composition and properties of the employed metal salts are of rather marginal importance therein. Another option for producing the oligomerization catalysts is that of mixing the corresponding individual components and granulation of the mixture with optional subsequent nickel application by impregnation.

The problem addressed by the present invention is that of providing a process with which an oligomerization catalyst having improved properties may be produced, wherein negative effects on the uptime of the catalyst and the mechanical properties such as strength are not permitted.

SUMMARY

It has now been found that, surprisingly, the problem addressed is solved with a process for producing an oligomerization catalyst in which the amorphous silica-alumina support material is employed in the ammonium form. A catalyst produced with support material in the ammonium form results in higher conversions and in higher selectivities for linear products when it is employed in the oligomerization.

DETAILED DESCRIPTION

The process according to the invention for producing an oligomerization catalyst comprising nickel oxide on an amorphous silica-alumina support material comprises the steps of:

a) mixing an amorphous silica-alumina support material comprising 10% to 20% by weight of $Al_2O_3$ and 80% to 90% by weight of $SiO_2$, an Al-containing and Si-free or Al-free and Si-containing binder and optionally at least a portion of a nickel source which is an aqueous, ammonia-free nickel solution of a nickel compound, an aqueous, ammonia-free nickel paste of a nickel compound or a combination of the abovementioned nickel solution and the abovementioned nickel paste, wherein the nickel compound is selected from the group consisting of nickel nitrate $(Ni(NO_3)_2)$, nickel acetate $(Ni(ac)_2)$, nickel acetylacetonate $(Ni(acac)_2)$, nickel sulfate $(NiSO_4)$, Nichols citrate or nickel carbonate $(NiCO_3)$, and granulating the resulting mixture;

b) treating the granulate produced in step a) with at least a portion of a nickel source as defined for step a) provided that the entirety of the nickel source has not already been mixed with the amorphous silica-alumina support material and the binder in step a); and c) calcining the granulate to produce the oligomerization catalyst;

characterized in that the amorphous silica-alumina support material in step a) is in the ammonia form.

In the context of the present invention the term "ammonia form" is to be understood as meaning a particular masking of the acid centres in the amorphous silica-alumina support material. The structure of the silica-alumina support material, in particular of aluminosilicates, typically consists of $SiO_4$ tetrahedra and $AlO_4$ tetrahedra. However in the case of aluminium atoms the outward-facing surface of this structure is missing the oxygen of an adjoining tetrahedron. The aluminium atom therefore formally has only a trivalent coordination with a free orbital (not shown here). The term "ammonium form" is to be understood as meaning the state where an ammonia molecule forms an adduct with the free orbital and formally forms an ammonium molecule with the hydrogen of an adjacent group (see left-hand side structure of the figure which follows). By contrast, the term "H form" is to be understood as meaning the state where an oxygen of an adjacent group forms an adduct with the free orbital, thus destabilizing the O—H bond and formally allowing a proton ($H^+$) to be eliminated (see right-hand side structure of the figure which follows).

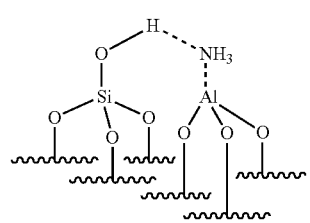

-continued

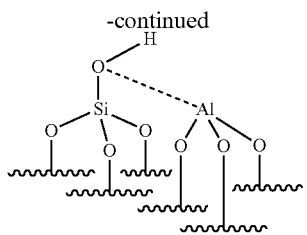

The amorphous silica-alumina support material is an amorphous aluminosilicate. In the context of the present invention "amorphous" is to be understood as meaning the property of a solid which results from the fact that the solid has no crystal structure, i.e. no long-range order.

However, it cannot be ruled out in the context of the present invention that the amorphous silica-alumina support material has small crystalline domains. The amorphous silica-alumina support material is thus not a crystalline material, for example not a zeolitic material.

The silica-alumina support material is an amorphous aluminosilicate comprising 10% to 20% by weight, preferably 12% to 17% by weight, of $Al_2O_3$ and 80% to 90% by weight, preferably 83% to 88% by weight, of $SiO_2$. This relates to the composition without any sorbed compounds (for example water or ammonia) which are for example reported under the term loss on ignition in commercially available products. In a preferred embodiment the amorphous aluminosilicate employed as the silica-alumina support material may further preferably have a particle size (d50) in the range from 10 to 80 μm, preferably 15 to 75 μm, measured by laser diffraction, for example in a Malvern Mastersizer. The amorphous aluminosilicate employed as the silica-alumina support material moreover preferably has a specific surface area (calculated as BET) of 250 to 380 $m^2/g$, particularly preferably of 280 to 360 $m^2/g$, measured by nitrogen physisorption according to DIN-ISO 9277 (2014-01 version). The proportion of the silica-alumina support material in the total batch (total composition including any and all employed solvents such as water) in step a) may be 20% to 50% by weight, preferably 25% to 45% by weight, when the entirety of the nickel source is already added in step a). If the nickel source is partially added in step b) a sufficient amount of liquid to allow granulation should be added to the mixture in step a) by addition of a solvent, preferably water.

In one embodiment the binder likewise employed in step a) may be an Al-containing and Si-free binder (Si-free denotes: <0.1% by weight of Si in the total composition of the binder). The Al-containing and Si-free binder is preferably an oxidic aluminium material, preferably aluminium oxide, aluminium hydroxide or aluminium oxide hydroxide, particularly preferably boehmite. The Al-containing and Si-free binder is moreover preferably present not in solid form but rather in dissolved form, particularly preferably as a colloidal solution. In a preferred embodiment the solvent in which the Al-containing and Si-free binder, preferably aluminium oxide, aluminium hydroxide or aluminium oxide hydroxide, particularly preferably boehmite, is present in dissolved form, preferably as a colloidal solution, is a 1% by weight nitric acid solution. The Al-containing and Si-free binder is present in the solution, preferably the colloidal solution, in an amount in the range from 10% to 25% by weight, preferably 12% to 20% by weight, particularly preferably 14% to 18% by weight. The proportion of the Al-containing and Si-free binder in the total batch (total composition including any and all employed solvents such as water) in step a) may be 10% to 30% by weight, preferably 15% to 25% by weight, when the entirety of the nickel source is already added in step a). If the nickel source were to be partially or completely added only in step b) the proportion of the Al-containing and Si-free binder in the total batch (total composition including any and all employed solvents such as water) in step a) is preferably 15% to 50% by weight, particularly preferably 25% to 40% by weight.

In a further embodiment the binder likewise employed in step a) may be an Al-free and Si-containing binder (Al-free denotes: <0.1% by weight of Al in the total composition of the binder). The Al-free and Si-containing binder is preferably silicon dioxide. The Al-free and Si-containing binder is moreover preferably present not in solid form but rather in the form of a colloidal dispersion, particularly preferably a silica sol. In a preferred embodiment the solvent in which the Al-free and Si-containing Binder, preferably the silicon dioxide, is dispersed is water. The Al-free and Si-containing binder, preferably the silicon dioxide, is present in the dispersion in an amount in the range from 7% to 50% by weight, preferably 12% to 42% by weight, particularly preferably 20% to 35% by weight. The average particle size of the Al-free and Si-containing binder, preferably of the silicon dioxide, may be 5 to 20 nm, preferably 6 to 10 nm, particularly in the dispersion (determinable by light scattering methods). The viscosity of the dispersion comprising the Al-free and Si-containing binder, preferably the silicon dioxide, may be in the range from 1 to 50 mPas, preferably 5 to 25 mPas. The dispersion comprising the Al-free and Si-containing binder, preferably the silicon dioxide, may further preferably have a pH in the range from 7 to 12, preferably 8 to 10. The density of the dispersion comprising the Al-free and Si-containing binder, preferably the silicon dioxide, is preferably 1 to 1.3 $g/cm^3$, particularly preferably 1.1 to 1.25 $g/cm^3$. The proportion of the Al-free and Si-containing binder in the total batch (total composition including any and all employed solvents such as water) in step a) and optionally b) may be 0.5% to 15% by weight, preferably 1% to 10% by weight.

It is also possible to add to the mixture in step a) an alkali metal compound, preferably a sodium compound. The sodium compound is preferably a sodium salt, particularly preferably sodium carbonate ($Na_2CO_3$). In a particularly preferred embodiment the sodium carbonate is added as an aqueous solution. The amount of sodium carbonate (in undissolved form) in the total batch (total composition of any and all employed solvents such as water, i.e. also including any water used to dissolve the sodium carbonate) in step a) and optionally b) of the production process may be between 0.01% and 2.5% by weight, preferably 0.05% and 2% by weight.

The nickel source employed in step a) or b) may in principle be any soluble nickel compound. Included among these are nickel nitrate ($Ni(NO_3)_2$), nickel acetate ($Ni(ac)_2$), nickel acetylacetonate ($Ni(acac)_2$), nickel sulfate ($NiSO_4$), nickel citrate or nickel carbonate ($NiCO_3$). Preference is given to nickel nitrate ($Ni(NO_3)_2$), nickel sulfate ($NiSO_4$) and nickel carbonate ($NiCO_3$). Employed nickel sources include aqueous, ammonia-free solutions of the abovementioned nickel compounds, aqueous, ammonia-free pastes of the abovementioned nickel compounds or a combination of the abovementioned nickel solution and the abovementioned nickel paste. In the context of the present invention "ammonia-free" is to be understood as meaning that the nickel source is substantially free from ammonia and at most contains ammonia as impurities. No ammonia is added to the nickel source in the form of a solution or paste. The aqueous, ammonia-free nickel paste contains water and the nickel paste according to the present invention contains less water than the nickel solution (when the same amount of nickel compound is assumed). Nickel paste is in principle a moistened solid composed of a nickel compound which is incompletely hydrated and in which hydroxidic nickel compounds are formally also formed; in the case of nickel carbonate for example $NiCO_3*Ni(OH)_2$ but also nonstoichiometric nickel carbonate hydroxides. In a preferred embodiment the aqueous, ammonia-free nickel paste contains between 30% and 50% by weight, preferably 35% to 45% by weight, of nickel based on the total weight of the paste. The aqueous, ammonia-free nickel solution may contain nickel in an amount in the range from 1% to 20% by weight, preferably 5% to 15% by weight, in each case based on the total weight of the solution.

In a preferred embodiment an aqueous, ammonia-free $Ni(CO_3)$— or $Ni(NO_3)_2$ solution is used as the nickel solution. The nickel content in the nickel solution may be from 1% to 20% by weight, preferably 5 to 15% by weight. It is preferable when a paste composed of nickel carbonate and water as solvent, wherein the nickel is present as carbonate/hydroxide (general empirical formula $NiCO_3*Ni(OH)_2$ but nonstoichiometric nickel carbonate hydroxides may also be formed), is used as the nickel paste. The paste may have a nickel content in the range from 30% to 50% by weight, preferably 35% to 45% by weight.

In an alternative embodiment the production of the oligomerization catalyst (step a) and/or optionally b)) employs both a Ni solution and a nickel carbonate paste. This is to be understood as meaning that when the addition of the nickel source is carried out exclusively in the abovementioned step a) the nickel source may be added both in the form of a paste and in the form of a solution. This is also to be understood as meaning that when the addition of the nickel source is carried out only partially or not at all in step a) but rather at least partially in step b) the nickel source may be added in the form of a paste in one step (a or b) and in the form of a solution in the other step (a or b) or may be added both in the form of a paste and in the form of a solution in both steps (a or b).

The total amount of nickel source (aqueous, ammonia-free paste and/or aqueous, ammonia-free solution) in the total batch (total composition of any and all employed solvents such as water) in step a) and optionally b) of the production process may be between 30% and 50% by weight, preferably 35% and 45% by weight.

The process according to the invention has the particular feature that no titanium dioxide and no zirconium dioxide are added but rather the oligomerization catalyst is produced without addition of titanium dioxide and zirconium dioxide. Any incidences of titanium dioxide and/or zirconium dioxide in the total composition of the oligomerization catalyst are due to impurities/trace incidences in the employed components.

In step a) the individual components, i.e. the amorphous silica-alumina support material, the binder and optionally the nickel source, are mixed with one another in a mixing vessel using an agitator and simultaneously or subsequently granulated. This may be effected using an intensive mixer for example. Mixing and granulation may typically be performed at ambient pressure. The temperature at which mixing and granulation may be carried out is preferably in the range from 10° C. to 60° C. The duration of process step a), i.e. of mixing and granulation, is between 5 minutes and 1 hour, preferably between 10 and 30 minutes.

In optional step b) the remaining portion of the nickel source, preferably in the form of a Ni solution, is added to the granulate produced in step a) and mixed with the granulate in order to treat the granulate with nickel. If at least a portion of the nickel source is to be added in step b) the possibly moist granulate from step a) may be dried prior to the treatment with the nickel source. The drying temperature may be 80° C. to 250° C., preferably 100° C. to 220° C.

The granulate resulting from step a) and/or step b) may still contain at least a portion of the employed solvent, i.e. in particular water. A moist granulate may therefore be concerned. Before the possibly still moist granulate is subjected to the calcination in step c) the moist granulate may be screened, preferably with a screen having a mesh size of 0.1 to 1.5 mm. The screened-off portion of the granulate (undersize) may be recycled back to step a) of the granulation.

After the mixing and granulating in step a), optionally after the treating (impregnating) of a granulate with at least a portion of a nickel source in step b) and optionally after the screening of the moist granulate the granulate may initially be dried in step c). This may be effected using known apparatuses such as for example belt dryers or the like. The drying temperature may be in the range from 80° C. to 250° C., preferably in the range from 100° C. to 220° C.

Before the optionally dried granulate is subjected to the calcination the dried granulate may be fractionated in order to establish a particular particle size of the granulate. Such a fractionation may be achieved for example through the use of at least one screen having a defined mesh size. In a particularly preferred embodiment two screens are used, wherein the one screen has a mesh size of 0.1 to 1.5 mm and the other screen has a mesh size of 2.5 to 7 mm. The remaining fractions (oversize and undersize) may be recycled to step a) optionally after preceding milling.

The optional drying and possible fractionation of the granulate is followed by the calcination of the granulate. This may comprise heating the granulate in a suitable furnace, preferably in a nitrogen stream, particularly preferably in a nitrogen countercurrent. Air may be added to the nitrogen stream during the calcination, wherein the amount of air supplied may be 100 to 10 000 ppm by volume, preferably 300 to 7000 ppm by volume. The calcination temperature may be 400° C. to 800° C., preferably 450° C. to 700° C., particularly preferably 500° C. to 600° C. This temperature may be maintained over several hours, preferably 5 to 20 hours, particularly preferably 8 to 15 hours, before the granulate is cooled. Air may be introduced into the furnace during cooling but the amount of air introduced should be controlled. The amount of the air optionally supplied is 100 to 10 000 ppm by volume, preferably 300 to 7000 ppm by volume.

The cooled granulate/the finished oligomerization catalyst may possibly then be fractionated once again to establish a particular particle size of the cooled granulate. Such a fractionation may be achieved for example through the use of at least one screen having a defined mesh size. In a particularly preferred embodiment two screens are used, wherein one screen has a mesh size of 0.1 to 1.5 mm and the other screen has a mesh size of 2.5 to 7 mm. The remaining fractions (oversize and undersize) may be recycled to step a) optionally after preceding milling.

After the last process step, of calcination and subsequent fractionation after cooling, the thus-produced oligomerization catalyst has a final total composition of 15% to 40% by weight, preferably 15% to 30% by weight, of NiO, 10% to 30% by weight of $Al_2O_3$, 55% to 70% by weight of $SiO_2$ and 0.01% to 2.5% by weight, preferably 0.05% to 2% by weight, of an alkali metal oxide. The figures are based on a total composition of 100% by weight. In a particularly preferred embodiment of the present invention, the oligomerization catalyst is substantially free from titanium dioxide and/or zirconium dioxide, the oligomerization catalyst in particular comprising less than 0.5% by weight, preferably less than 0.1% by weight, particularly preferably less than 0.01% by weight, of titanium dioxide and/or zirconium dioxide in its total composition.

In a preferred embodiment the oligomerization catalyst produced according to the invention has a nickel dispersity expressed as the chemisorbed amount of CO of more than 30 µmol/g, preferably more than 33 µmol/g, particularly preferably more than 36 µmol/g.

The state of subdivision of nickel on the surface may be determined via the chemisorption of carbon monoxide (CO). To this end the sample is initially reduced with hydrogen in a first step. CO is then passed over the sample until no more CO is taken up by the sample. The thus determined amount of chemisorbed CO makes it possible to estimate the fineness of the state of subdivision of the nickel on the surface. The finer the state of subdivision of the nickel, the more CO can be taken up. In the case of large nickel crystals, i.e. a relatively disadvantageous state of subdivision of nickel, the nickel atoms inside the crystal are not accessible to the CO. It is therefore the case that the finer the state of subdivision of nickel on the surface the more CO can be bound for an identical total amount of nickel. Measurement was performed as follows:

0.2 g of each sample were filled into the sample vessel of the Thermo Scientific TPDRO 1100 instrument. To ensure the presence of elemental nickel at the surface the sample was reduced with hydrogen. To this end 20 ml/min of argon comprising a proportion of hydrogen of 5% were passed over the sample and heated from room temperature to 520° C. and held for 30 min. After leaving the sample vessel the gas was passed over a molecular sieve baked-out prior to the measurement for adsorption of water.

After the reduction the sample was cooled to room temperature under inert gas and CO chemisorption was commenced. To this end respective portions of 366 µL of CO gas were passed over the sample at 10 min intervals. Chemisorption of CO onto nickel changes the thermal conductivity of the gas, thus allowing quantification of the chemisorbed amount of CO. CO was passed over the sample in pulses until 5 consecutive pulses showed no change in thermal conductivity, i.e. CO is no longer taken up.

The oligomerization catalyst produced according to the invention may have a specific surface area (calculated according to BET) of 150 to 400 $m^2/g$, preferably 190 to 350 $m^2/g$, particularly preferably of 220 to 330 $m^2/g$. The BET surface area is measured by nitrogen physisorption according to DIN ISO 9277 (2014-01 version).

In a further preferred embodiment the oligomerization catalyst produced with the process according to the invention comprises mesopores and macropores, i.e. has a bimodal pore size distribution. The mesopores of the oligomerization catalyst according to the invention have an average pore diameter of 5 to 15 nm, preferably of 7 to 14 nm, particularly preferably of 9 to 13 nm. By contrast the macropores of the oligomerization catalyst according to the invention preferably have an average pore diameter of 1 to 100 µm, particularly preferably of 2 to 50 µm. The average pore volume of the oligomerization catalyst according to the invention, i.e. of both the mesopores and the macropores, may be 0.5 to 1.5 $cm^3/g$, preferably 0.7 to 1.3 $cm^3/g$. The average pore diameter and the average pore volume may be determined by mercury porosimetry according to DIN 66133 (1993-06 version).

Furthermore, the oligomerization catalyst produced by the process according to the invention may have an average particle diameter (d50) of 0.1 mm to 7 mm, preferably 0.5 to 6 mm, particularly preferably of 1 mm to 5 mm. The average particle diameter may be determined by imaging methods, in particular by those in the standards ISO 13322-1 (2004-12-01 version) and ISO 13322-2 (2006-11-01 version). A suitable instrument for analysis of particle diameter is for example the Camsizer 2006 instrument (Retsch Technology).

The catalyst produced with the process according to the invention may be used in particular for the oligomerization of C3- to C6-olefins, preferably C3- to C5-olefins, particularly preferably C4-olefins, or olefin-containing input mixtures based thereupon. The olefins or olefin-containing input mixtures are employed as a reactant stream.

The present invention also provides a process for oligomerization of C3- to C6-olefins, wherein olefin-containing input mixture containing the C3- to C6-olefins is passed over a catalyst in at least one reaction zone, wherein the oligomerization catalyst produced according to the invention is used for catalysis of the oligomerization reaction. According to the invention a reaction zone comprises at least one reactor and at least one distillation column in which the oligomers formed may be separated. The process according to the invention may also be operated with two or more reaction zones. The oligomerization is preferably carried out in the liquid phase.

Olefins employable for the process according to the invention include C3- to C6-olefins, preferably C3- to C5-olefins, particularly preferably C4-olefins, or olefin-containing input mixtures based thereupon which may also contain proportions of analogous alkanes. Suitable olefins are inter alia α-olefins, n-olefins and cycloalkenes. The olefins used as reactants are preferably n-olefins. In a particularly preferred embodiment, the olefin is n-butene. According to the invention the term "olefin-containing input mixtures based thereupon" is to be understood as encompassing any type of mixtures containing the relevant C3- to C6-olefins to be oligomerized in an amount which makes it possible to perform the oligomerization. The olefin-containing input mixtures preferably contain practically no further unsaturated compounds and polyunsaturated compounds such as dienes or acetylene derivatives. It is preferable to employ olefin-containing input mixtures containing less than 5% by weight, in particular less than 2% by weight, of branched olefins based on the olefin proportion. Also preferably employed are olefin-containing input mixtures containing less than 2% by weight of branched olefins, in particular iso-olefins.

Propylene (C3) is produced on a large industrial scale by cracking of naphtha and is a commodity chemical which is readily available. C5-olefins are present in light petroleum fractions from refineries or crackers. Technical mixtures which contain linear C4-olefins are light petroleum fractions from refineries, C4-fractions from FC crackers or steam crackers, mixtures from Fischer-Tropsch syntheses, mixtures from the dehydrogenation of butanes, and mixtures formed by metathesis or from other industrial processes. Mixtures of linear butenes suitable for the process according to the invention are obtainable for example from the C4-fraction of a steam cracker. Butadiene is removed in the first step here. This is accomplished either by extraction or extractive distillation of the butadiene or by selective hydrogenation thereof. In both cases a virtually butadiene-free C4-cut is obtained, namely raffinate 1. In the second step, isobutene is removed from the C4-stream, for example by production of methyl tert-butyl ether (MTBE) by reaction with methanol. Other options include the reaction of the isobutene from the raffinate I with water to afford tert-butanol or the acid-catalysed oligomerization of isobutene to afford diisobutene. As desired, the now isobutene-free C4-cut, raffinate II, contains the linear butenes and any butanes. The 1-butene may optionally still be removed by distillation. Both fractions, the one comprising but-1-ene or the one comprising but-2-ene, may be used in the process according to the invention.

In a further preferred embodiment C4-olefin-containing material streams are supplied to the process as olefin-containing input mixtures. Suitable olefin-containing input mixtures include inter alia raffinate I (butadiene-free C4-cut from a steam cracker) and raffinate II (butadiene-free and isobutene-free C4-cut from a steam cracker).

A further option for producing a suitable olefin mixture is that of subjecting raffinate I, raffinate II or a similarly constituted hydrocarbon mixture to hydroisomerization in a reactive column. This may afford inter alia a mixture consisting of 2-butenes, small proportions of 1-butene and possibly n-butane and also isobutane and isobutene.

The oligomerization is generally carried out at a temperature in the range from 50° C. to 200° C., by preference 60° C. to 180° C., preferably in the range from 60° C. to 130° C., and at a pressure of 10 to 70 bar, preferably of 20 to 55 bar. If the oligomerization is to be carried out in the liquid phase the parameters pressure and temperature must to this end be chosen such that the reactant stream (the employed olefins or olefin mixtures) is in the liquid phase. The weight-based space velocities (reactant mass per unit catalyst mass per unit time; weight hourly space velocity (WHSV)) are in the range between 1 g of reactant per g of catalyst and per h (=1 h$^{-1}$) and 190 h$^{-1}$, preferably between 2 h$^{-1}$ and 35 h$^{-1}$, particularly preferably between 3 h$^{-1}$ and 25 h$^{-1}$.

In one embodiment, the degree of dimerization (also referred to as "percentage selectivity based on dimerization") after the oligomerization based on the converted reactant is at least 60%, more preferably at least 75%, particularly preferably at least 80%.

The linearity of an oligomerization product/of the dimers formed is described by the ISO index and represents a value for the average number of methyl branches in the dimer. For example (for butene as the reactant), n-octenes contribute 0, methylheptenes contribute 1 and dimethylhexenes contribute 2 to the ISO index of a C8 fraction. The lower the ISO index, the more linear the construction of the molecules in the respective fraction. The ISO index is calculated by the following general formula:

$$\frac{\left(\begin{array}{l}\text{singly branched dimers (\% by weight)} + \\ 2 \times \text{doubly branched dimers (\% by weight)}\end{array}\right)}{100}$$

Accordingly, a dimer mixture having an ISO index of 1.0 has an average of exactly one methyl branch per dimeric molecule.

The ISO index of the product from the oligomerization process according to the invention is preferably 0.8 to 1.2, more preferably 0.8 to 1.18.

The oligomers produced by the process according to the invention are utilized inter alia for producing aldehydes, alcohols and carboxylic acids. Thus for example the dimerizate of linear butenes affords a nonanal mixture by hydroformylation. This provides either the corresponding carboxylic acids by oxidation or a C9-alcohol mixture by hydrogenation. The C9-acid mixture may be used for producing lubricants or siccatives. The C9-alcohol mixture is a precursor for the production of plasticizers, particularly dinonyl phthalates, or DINCH.

Even without further elaboration it is assumed that a person skilled in the art will be able to utilize the description above to the greatest possible extent. The preferred embodiments and examples are therefore to be interpreted merely as a descriptive disclosure which is by no means limiting in any way whatsoever.

The present invention is more particularly elucidated hereinbelow with reference to examples. Alternative embodiments of the present invention are obtainable analogously.

EXAMPLES

A commercially available amorphous aluminosilicate was initially (virtually) completely converted into the ammonium form by admixing with an excess of ammonium-containing solution and subsequent drying at 100° C. to 120° C., i.e. it was ensured that all acid centres were masked by ammonium ions.

Catalyst 1 (Inventive):

A binder (colloidal solution comprising silicon dioxide, SiO$_2$ content between about 30% by weight) and the amorphous aluminosilicate were placed in the mixing vessel of an intensive mixer and stirred. Stirring was stopped as soon as granulates having a suitable particle diameter (0.1 mm to 7 mm) are obtained. The thus obtained granulate was dried at about 120° C. and subsequently screened using two screens to remove excessively small or excessively large particles from the granulate.

The dry granulate was subsequently impregnated with an aqueous Ni(NO$_3$)$_2$ solution (Ni content between 10% and 12.5% by weight). The granulate is then calcined in a furnace. For the calcination the granulate is heated to a temperature between 500° C. to 600° C. and this temperature is maintained for about 10 to 12 hours. The furnace filled with granulate has nitrogen flowing through it and a ratio of volumes of granulate to volumes of nitrogen per hour (standard volumes) of at least 1:1000 is maintained. During the cooling of the granulate to room temperature about 6000 ppm by volume of air were metered into the nitrogen stream. The cooled granulate corresponds to the finished oligomerization catalyst.

Catalyst 2 (Noninventive):

To produce catalyst 2 the initially produced aluminosilicate in ammonium form was calcined at 400° C. This drove out a portion of the ammonium cations which masked the acid centres. The aluminosilicate used for producing the catalyst is thus partially in the H form.

The production of catalyst 2 was then performed as per claim 1 with the exception that the aluminosilicate is—as mentioned—partially in the H form.

Catalyst 3 (Noninventive):

To produce catalyst 3 the initially produced aluminosilicate in ammonium form was calcined at 550° C. This drove out the entirety of the ammonium cations which masked the acid centres. The aluminosilicate used for producing the catalyst is thus virtually completely in the H form.

The production of catalyst 2 was then performed as per claim 1 with the exception that the aluminosilicate is—as mentioned—completely in the H form.

Use of the Catalysts in the Oligomerization:

About 12 g of the catalyst in each case were introduced into a metal tube having an internal diameter of 6 mm. Added in front of and behind the catalyst were glass beads having a diameter of 2 mm, which serve as a pre-heating and cooling phase. The oligomerization was performed using a butene/butane mixture comprising 80% n-butenes at 30 bar and a loading of 7.5 g/h of butene per gram of catalyst, wherein the reaction temperature was varied between 80° C. and 100° C. The products were analysed by gas chromatography for the conversion of butenes and the linearity of the octenes.

The conversions and selectivities achieved as a function of temperature for catalyst 1 (inventive) and the noninventive catalysts 2 and 3 and also the ISO indices resulting therefrom are reported in tables 1 to 3.

TABLE 1

Conversions and ISO indices in oligomerization using catalyst 1
Loading (feed of C4-olefins in g/h per unit mass of catalyst in g) as WHSV: 7.5 h$^{-1}$

|  | Temperature | Conversion based on C4-olefins | ISO index |
|---|---|---|---|
| Catalyst 1 (inventive) | 80° C. | 37.4% | 1.18 |
|  | 90° C. | 40.3% | 1.18 |
|  | 100° C. | 45.6% | 1.16 |

TABLE 2

Conversions and ISO indices in oligomerization using catalyst 2
Loading (feed of C4-olefins in g/h per unit mass of catalyst in g) as WHSV: 7.5 h$^{-1}$

|  | Temperature | Conversion based on C4-olefins | ISO index |
|---|---|---|---|
| Catalyst 2 (noninventive) | 80° C. | 27.1% | 1.20 |
|  | 90° C. | 29.9% | 1.21 |
|  | 100° C. | 33.9% | 1.23 |

TABLE 3

Conversions and ISO indices in oligomerization using catalyst 3
Loading (feed of C4-olefins in g/h per unit mass of catalyst in g) as WHSV: 7.5 h$^{-1}$

|  | Temperature | Conversion based on C4-olefins | ISO index |
|---|---|---|---|
| Catalyst 3 (noninventive) | 80° C. | 20.7% | 1.30 |
|  | 90° C. | 19.4% | 1.33 |
|  | 100° C. | 30.0% | 1.37 |

It is apparent that, surprisingly, the use of the amorphous aluminosilicate in the ammonium form in the production of the catalyst resulted in markedly improved conversions and lower iso-indices for the product mixture.

The invention claimed is:

1. A process for producing an oligomerization catalyst, comprising at least the steps of:
   a) mixing an amorphous silica-alumina support material comprising from 10% to 20% by weight of $Al_2O_3$ and from 80% to 90% by weight of $SiO_2$, an Al-containing and Si-free or Al-free and Si-containing binder, at least a portion of a nickel source comprising an aqueous, ammonia-free nickel solution of a nickel compound, an aqueous, ammonia-free nickel paste of a nickel compound or a combination of the abovementioned nickel solution and the abovementioned nickel paste, wherein the nickel compound is selected from the group consisting of nickel nitrate ($Ni(NO_3)_2$), nickel acetate ($Ni(ac)_2$), nickel acetylacetonate ($Ni(acac)_2$), nickel sulfate ($NiSO_4$), nickel citrate or nickel carbonate ($NiCO_3$), and granulating the resulting mixture, wherein the amorphous silica-alumina support material in step a) is in the ammonia form;
   b) treating the granulate produced in step a) with at least another portion of a nickel source as defined for step a); and
   c) calcining the granulate to produce the oligomerization catalyst.

2. The process according to claim 1, wherein step a) comprises employing an oxidic aluminum material as the Al-containing and Si-free binder or silicon dioxide as the Al-free and Si-containing bind.

3. The process according to claim 2, wherein the oxidic aluminum is selected from the group consisting of aluminum oxide, aluminum hydroxide and aluminum oxide hydroxide.

4. The process according to claim 3, wherein the nickel source of step a) and/or b) comprises the aqueous, ammonia-free nickel paste which comprises between 30% and 50% by weight of nickel based on the total weight of the nickel paste.

5. The process according to claim 3, wherein the nickel source of step a) and/or b) comprises the aqueous, ammonia-free nickel solution which comprises nickel in an amount in the range of from $_1$% to $^2$0% by weight based on the total weight of the solution.

6. The process according to claim 3, wherein the calcination in step c) is performed at a temperature between 400° C. and 800° C.

7. The process according to claim 3, wherein the oligomerization catalyst has a final composition of from 15% to 30% by weight of NiO, from 10% to 30% by weight of $Al_2O_3$, from 55% to 70% by weight of $SiO_2$ and optionally from 0.01% to 2.5% by weight of an alkali metal oxide.

8. A process for oligomerization of C3- to C6-olefins comprising contacting an olefin-containing feed mixture containing the C3- to C6-olefins with a catalyst comprising the oligomerization catalyst of claim 3 in a reaction zone.

9. The process according to claim 1, wherein the nickel source of step a) and/or b) comprises the aqueous, ammonia-free nickel paste which comprises between 30% and 50% by weight of nickel based on the total weight of the nickel paste.

10. The process according to claim 9, wherein the paste is composed of nickel carbonate and water as solvent, wherein the nickel is present as carbonate/hydroxide.

11. The process according to claim 1, wherein the nickel source of step a) and/or b) comprises the aqueous, ammonia-free nickel solution which comprises nickel in an amount in the range of from 1% to 20% by weight based on the total weight of the solution.

12. The process according to claim 11, wherein $Ni(CO_3$ or $Ni(NO_3)_2$ solution is used as the aqueous, ammonia-free nickel solution.

13. The process according to claim 11, wherein the calcination in step c) is performed in a nitrogen stream.

14. The process according to claim 1, wherein the calcination in step c) is performed at a temperature between 400° C. and 800° C.

15. The process according to claim 1, wherein the oligomerization catalyst has a final composition of from 15% to 40% by weight of NiO, from 10% to 30% by weight of $Al_2O_3$, from 55% to 70% by weight of $SiO_2$ and optionally from 0.01% to 2.5% by weight of an alkali metal oxide.

16. The process according to claim 1, wherein an alkali metal is added in step a) such that the oligomerization catalyst has a final composition of from 15% to 30% by weight of NiO and from 0.01% to 2.5% by weight of an alkali metal oxide.

17. A process for oligomerization of C3- to C6-olefins comprising contacting an olefin-containing feed mixture containing the C3- to C6-olefins with a catalyst comprising the oligomerization catalyst of claim 1 in a reaction zone.

18. The process for oligomerization according to claim 17, wherein the olefin-containing feed mixture contains less than 2% by weight of branched olefins.

19. The process for oligomerization according to claim 17, wherein the contacting takes place in the liquid phase.

20. The process for oligomerization according to claim 17, wherein the contacting is carried out at a pressure of 10 to 70 bar and a temperature of from 50° C. to 200° C., wherein if the contacting is carried out in the liquid phase, the pressure and temperature are chosen such that the olefin-containing feed mixture is in the liquid phase.

* * * * *

UNITED STATES PATENT AND TRADEMARK OFFICE
CERTIFICATE OF CORRECTION

Page 1 of 1

PATENT NO. : 10,882,027 B2
APPLICATION NO. : 16/293702
DATED : January 5, 2021
INVENTOR(S) : Nadolny et al.

It is certified that error appears in the above-identified patent and that said Letters Patent is hereby corrected as shown below:

In the Claims

Column 12,
Line 63, "wherein Ni(CO$_3$or" should read -- wherein Ni(CO$_3$) or --.

Signed and Sealed this
Sixteenth Day of February, 2021

Drew Hirshfeld
*Performing the Functions and Duties of the
Under Secretary of Commerce for Intellectual Property and
Director of the United States Patent and Trademark Office*